United States Patent
Kodama et al.

(10) Patent No.: US 6,419,926 B2
(45) Date of Patent: Jul. 16, 2002

(54) SPECIFIC ANTIBODIES FOR USE IN PREPARATION OF PHARMACEUTICAL COMPOSITIONS USEFUL IN THE PREVENTION OR TREATMENT OF GASTRITIS, GASTRIC ULCERS AND DUODENAL ULCERS

(75) Inventors: Yoshikatsu Kodama; Faustino C. Icatlo, Jr., both of Gifu; Nobutake Kimura; Masato Ariga, both of Saitama-ken, all of (JP)

(73) Assignees: Ghen Corporation, Gifu; Nisshin Pharma Inc., Tokyo, both of (JP)

( * ) Notice: Subject to any disclaimer, the term of this patent is extended or adjusted under 35 U.S.C. 154(b) by 0 days.

(21) Appl. No.: 09/056,649

(22) Filed: Apr. 8, 1998

(30) Foreign Application Priority Data

Apr. 11, 1997 (JP) .............................. 9-094159

(51) Int. Cl.⁷ ........................................... A61K 39/395
(52) U.S. Cl. ................ 424/157.1; 424/93.4; 424/93.45; 424/164.1
(58) Field of Search ........................... 424/164.1, 157.1, 424/93.4, 93.45

(56) References Cited

U.S. PATENT DOCUMENTS 4,748,018 A * 5/1988 Stolle et al. ............. 424/157.1

(List continued on next page.)

FOREIGN PATENT DOCUMENTS

| EP | 0 484 148 A1 | 5/1992 | | |
|----|----|----|----|----|
| EP | 0 752 473 A3 | 3/1997 | | |
| JP | 4-169539 | 6/1992 | | |
| JP | 4-275232 | 9/1992 | | |
| JP | 4-330099 | 11/1992 | | |
| WO | 90/04030 | * of 1990 | | |
| WO | 93/07273 | * of 1993 | | |
| WO | 93/20843 | * of 1993 | | |
| WO | 94/26901 | * of 1994 | | |
| WO | 94/06474 | * 3/1994 | | |
| WO | WO 94/21284 | 9/1994 | | |
| WO | 95/22987 | * 8/1995 | .......... A61K/39/00 |
| WO | 95/33482 | * 12/1995 | | |
| WO | 97/03360 | * 1/1997 | | |
| WO | 9721103 | * 6/1997 | | |

OTHER PUBLICATIONS

Kim et al (1997), Korean Journal of App. Microbiol & Biotech., Dec., vol. 25(6), p. 612–616 (abstract).*
Hassl et al (1988), J. Immunol. Methods, vol. 110, p. 225–228.*

(List continued on next page.)

Primary Examiner—Jennifer E. Graser
Assistant Examiner—Ginny Allen Portner
(74) Attorney, Agent, or Firm—Burns, Doane, Swecker & Mathis, LLP (57) ABSTRACT

The present invention provides specific antibodies obtained from eggs laid by hens which have been immunized against urease of Helicobacter pylori as an antigen, and specific antibodies obtained from eggs laid by hens which have been immunized against flagella of Helicobacter pylori as an antigen. These antibodies are useful for the prevention or treatment of gastritis, gastric ulcers and duodenal ulcers caused by infection of Helicobacter pylori. At least one organism selected from lactic acid bacteria, Enterococcuses, yeasts, and Baillus can be used along with the antibodies.

17 Claims, 3 Drawing Sheets

U.S. PATENT DOCUMENTS

| | | | | |
|---|---|---|---|---|
| 5,080,895 A | * | 1/1992 | Tokoro | 424/85.8 |
| 5,258,178 A | * | 11/1993 | Cordle et al. | 424/157.1 |
| 5,260,057 A | * | 11/1993 | Cordle et al. | 424/157.1 |
| 5,531,989 A | * | 7/1996 | Paul | 424/93.4 |
| 5,538,729 A | * | 7/1996 | Czinn | 424/234.1 |
| 5,578,302 A | * | 11/1996 | Brassart et al. | 424/93.45 |
| 5,585,098 A | * | 12/1996 | Coleman | 424/157.1 |
| 5,610,060 A | * | 3/1997 | Ward et al. | 435/252.1 |
| 5,741,489 A | * | 4/1998 | Pimental | 424/157.1 |
| 5,744,134 A | * | 4/1998 | Paul | 424/93.4 |
| 5,871,731 A | * | 2/1999 | Sprotte et al. | 424/130.1 |
| 5,262,156 A | * | 3/2000 | Alemohammad | 424/92 |
| 6,039,959 A | * | 3/2000 | Burnie | 424/234.1 |
| 6,080,401 A | * | 6/2000 | Reddy et al. | 424/93.3 |
| 6,143,559 A | * | 11/2000 | Michael et al. | 435/328 |
| 6,180,099 B1 | * | 1/2001 | Paul | 424/93.4 |

OTHER PUBLICATIONS

Clyne, M et al, Infection and Immunity, vol. 64(7), pp. 2817–2820, Jul. 1996.*

Blanchard, T.G et al, Infection and Immunity, vol. 63(4), pp. 1394–1399, Apr. 1995.*

Kostrzynaka et al (1991), J. Bacteriol., Feb., vol. 173(3), p. 937–946.*

Leying et al (1992), Mol. Microbiol, vol. 6(19), p. 2863–2874.*

Thomas et al (1993), The Lancet, vol. 342, No. (8863), Jul. 10, p. 121.*

Ferrero et al, Microbial Ecology in Health and Disease, vol. 4, pp. 121–134, 1991.*

Pappo, J et al, Infection Immunity, vol. 63(4), pp. 1246–1252, Apr. 1995.*

Newell, D.G. Scand J Gastroenterol. vol. 26 (suppl.187), pp. 31–38, 1991.*

Davin, C et al, vol. 104(4), p A1035, col. 2, second abstract, 1993.*

Hawtin, P.R. et al, J General Microbiology, vol. 136 ,(10) pp. 1995–2000 1990.*

Czinn et al, Vaccine, vol. 11(6), pp. 637–642 Apr. 1993.*

Thomas, JE et al, Lancet, vol. 342(8863), p. 121 1993.*

Buknov et al (1994), Mol. Microbiol, vol. 11(3), p. 509–523.*

Malfertheiner et al (1993), Clinical Therapeutics, vol. 15 (suppl B), p. 37–48.*

Haas et al (1993), Mol. Microbiol, vol. 8(4), p. 753–760.*

Blaser (1993), Trends in Microbiol, vol. 1(7), Oct., p. 255–260.*

Gassman et al, (1990), Schweiza Archivfur Tierheilkunde, vol. 132(6) p. 289–294.*

Bade et al (1984), J. Immunol. Methods, vol. 172(2), p. 421–426, (abstract).*

Stacey, AF et al, European Journal of Clinical Microbiology and Infectious Disease, vol. 9(10), pp 732–737, (abstract) Oct. 1990.*

Thomas, JE et al, Journal of Clinical Mirobiology, vol. 30(5), pp. 1338–1340, (abstract) May 1992.*

Nagata, K etal, Infection Immunity, vol. 60(11), pp. 4826–4831, Nov. 1992.*

Emark, TH et al, FASEB Journal, vol.9(3), p. A216 (abstract0 1995.*

Zhang, J et al, Zhonghua Weishengwuxue He Mianyixue Zazhi, vol. 5(5), pp. 344–346 (abstract) 1995.*

Lee, CK et al, J. Infectious Disease, vol. 172(1), pp. 161–172, (abstract) Jul. 1995.*

Makoto, O et al, Kagaku, vol. 50(4), pp. 230–235, (abstract) 1995.*

Yokoyama, H et al, American Journal of Veterinary Research, Jun. 1993, vol. 54(6), pp. 867–872, (abstract) Jun. 1993.*

Otake, S et al, Journal of Dental Research, vol. 70(3), pp. 162(6), (abstract) Mar. 1991.*

Schade, R et al, Atla–Alternative to laboratoyr aminmals, vol. 19(4), pp. 403–419, (abstract) 1991.*

Hadge, D, Allergie and Immunologie, vol. 31(4), pp. 231–243, (abstrat) 1985.*

Deignan, T et al, 9th International Congress of Immunology, p. 892, (abstract) Jul. 1995.*

Yokoyama, H et al, Infection Immunity, vol. 60(3), pp. 998–1007, (abstract) Mar. 1992.*

Hajime, H etal, Japanese Journal of Dairy and Food Science, vol. 41(6), pp. 217–222, (abstract) 1992.*

Sugiyama, T, Nogyo Gijutsu Kenkyu, vol. 50(5), pp. 86–87, figure 2, (abstract) 1996.*

Schmidt, P et al, Zentralblatt fur Veterinarmedizin, vol. 36(8), pates 619–628, (abstract) Oct. 1989.*

O'Farrelly, C et al, Infection Immunity, vol. 60(7), pates 2593–2597, Jul. 1992.*

Hassl, A et al, J. Immunological Methods, vol. 110, pp. 225–228 1988.*

Akita, EM et al, J. Immunological Methods, vol. 162, pp. 155–164 1993.*

Larsson, A et al, Comp. Immun. Microbiol. Infect. Dis., vol. 13(4), pp. 199–201 1990.*

Seymour, C et al, Applied and Environmental Microbiology, Mar. 1994, vol. 60(3), pp. 1025–1028.*

Dewhirst, FE et al, International Journal of systematic bacteriology, Jul. 1994, vol. 44(3), pp. 553–560.*

Science, vol. 267, Mar. 17,1995, pp.1655–58, "Developments of a Mouse Model of *Helicobacter pylori* Infection That Mimics Human Disease".

ISSN 0002–1407, Nippon Nogiekagaku Kaishi, Mar. 1997. K.A. Eaton & S. Krakowka, pp. 434–437, "Avirulent, Urease–Deficient *Helicobacter pylori* Colonizes Gastric Epithelial Explants Ex Vivo".

Infection and Immunity, Jul. 1996, vol. 64, No. 7, pp. 2817–2820, "The Urease Enzyme of *Helicobacter pylori* Does Not Function as an Adhesin".

Journal of Clinical Mircobiology, Oct. 1989, pp. 2328–2330, "*Lactobacillus acidophilus* Inhibits Growth of *Campylobacter pylori* in Vitro".

Journal of Applied Bacteriology, 1995, 79, pp. 475–479, "In vitro inhibition of *Helicobacter pylori* NCTC 11637 by organic acids and lactic acid bacteria".

The Meeting of the 30th Japan Germ–free Animal Gnotobiology Society, Program and Abstracts, pp. 22, Requested Title 18, Jan. 1997, "New Attempt for Inhibiting *Helicobacter pylori*".

Katloff, K.L. "*Helicobactor pylori* and gastroduodenal disorders: new approaches for prevention, diagnosis and treatment", Vaccine, vol. 14, No. 12, 1996, pp. 1174–1175.

Patent Abstract of Japanese 09087297, vol. 97, No. 7, Jul. 31, 1997.

Patent Abstract of Japanese 04275232, vol. 17, No. 67, Feb. 10, 1993.

* cited by examiner

Fig. 2

SPECIFIC ANTIBODIES FOR USE IN PREPARATION OF PHARMACEUTICAL COMPOSITIONS USEFUL IN THE PREVENTION OR TREATMENT OF GASTRITIS, GASTRIC ULCERS AND DUODENAL ULCERS

BACKGROUND OF THE INVENTION

The present invention relates to specific antibodies for use in preparing pharmaceutical compositions useful for the prevention or treatment of gastritis, gastric ulcers and duodenal ulcers caused by infection of *Helicobacter pylori* (hereinafter referred to as *H. pylori* or Hp), and for use as an additive to foods useful for the prevention of gastritis, gastric ulcers and duodenal ulcers.

At present it is believed that eradication of *H. pylori* in the stomach is essential for treating peptic ulcers fully. The combination of antibiotics and suppressors of gastric acid secretion has been generally proposed as a therapy for effective eradication of *H. pylori* as described below.

*H. pylori* is a gram-negative spiral rod-shaped bacterium having some flagella at one end and inhabiting the human gastric mucosa. Marshall, B. J. and Warren, J. R. in Australia reported in 1983 that this bacterium was frequently detected in stomach biopsy specimens from patients with gastric ulcers. At that time this bacterium was named *Campylobacter pylory* since it resembles Campylobacter in morphology and growth characteristics. Later, it was found that the bacterium is different from Campylobacter in the fatty acid composition of its outer membrane and sequence of ribosome 16S-RNA. Therefore, the bacterium is now referred to as *Helicobacter pylori* and belongs to a newly established genus of Helicobacter.

Since then, many reports have been published based on epidemiological studies, indicating that this bacterium causes gastritis, gastric ulcers and duodenal ulcers and is associated with diseases such as gastric cancer. Once *H. pylori* colonizes gastric mucosa, it cannot be eradicated in the stomach and continues to inhabit the stomach, although the immune response to infection thereof is strong, i.e., the antibody titer is high. Therefore, unless *H. pylori* is completely eliminated from the stomach by antibiotic therapy, the condition of infection will return to the same level as before treatment within about a month after the administration of antibiotics is stopped. Additionally, the pH of the stomach is maintained very low by HC1, which is a strong acid, and therefore most antibiotics are apt to be inactivated. For this reason, the combination of an antibiotic and a proton pump inhibitor which strongly suppresses the secretion of gastric acid is utilized often in a greater dose than usual for eradication of *H. pylori*. Recently, a new treatment employing a combination of bismuth subsalicylate, metronidazole, and tetracycline has proved to have the highest rate of elimination of *H. pyroli*, but metronidazole in this combination is known to cause the rapid emergence of an antibiotic-resistant strain when used alone. In developing countries this medicine has been used widely for treating diarrhea patients, and as a result there is a high rated infection with metronidazole-resistant *H. pylori*. Thus, the administration of antibiotics for a long time has the serious problems of increasing antibiotic-resistant strains as well as causing side effects.

At present, an immunological therapy approach using an oral vaccine has been proposed in order to solve problems such as side effects and increase of antibiotic-resistant strains by treatment with antibiotics for the eradication of the bacteria. However, for this purpose it is essential to develop model animals for Hp infection. It has been reported that Hp infection tests have been conducted using rats, mice, rabbits, dogs, pigs, and monkeys, and tests using dogs, pigs and monkeys have been successful. However, Hp cannot easily infect small animals such as mice and rats, and infection tests require complicated conditions. For example, germ-free animals are required for infection or fresh isolates are required for maintaining infection for a long time. These requirements have obstructed studies aimed at developing new methods for prevention and treatment.

For example, it was reported by Marchetti,M. et al. in Science, vol. 267, pp1655–1658 (1995) that 80% of Hp infection was inhibited by oral immunization using a mouse model for evaluating the efficacy of Hp oral vaccine. However, this oral vaccine preparation had heat-labile toxin (LT) derived from *E. coli* as an adjuvant. Generally, in such experiments using an oral vaccine, the vaccine preparation has cholera toxin in addition to LT derived from *E. coli*, and mucosal immunity cannot be attained without these adjuvants. LT from *E. coli* and cholera toxin have a high level of toxicity, and this vaccine method has many unsolved problems in respect to safety in its practical application to humans. Also, the vaccine is predominantly used for prevention, and therefore it has no effect on patients who have already been infected with Hp.

As a new attempt to inhibit Hp, Aiba et al. (The Meeting of the 30th Japan Germ-free Animal Gnotobiology Society, Program and Abstracts, pp22, Requested Title 18, New Attempt for Inhibiting *Helicobacter pylori*, January 1997) used germ-free mice as a model of Hp infection and studied (i) the effect of *Lactobacillus salivarius* as probiotics on inhibition of Hp and (ii) the effect of oral administration of anti-Hp antibodies obtained from the yolk of the eggs of hens immunized with formalin-killed whole cell of Hp on inhibition of Hp. In case (i), the number of Hp in the stomach of the Hp infected mice in an administered group became 10–1000 times less than that of a control group. In case (ii), the number of Hp in the stomach of an administered group became 10 times less than that of a control group.

However, these results were obtained using mice which do not have normal flora in the oral cavity, stomach and intestines, and it is not expected that such results can be obtained in conventional mice having normal flora. Generally, when mice having inherent normal flora are inoculated with human lactic acid bacteria, the bacteria are eliminated by the normal flora and do not colonize. Also, the antibodies used in the above experiments were those against whole cells of Hp, and the number of Hp in the stomach became only 10 times less than that of the control group, i.e., Hp was not eliminated completely. Furthermore, there is no reference to the relation between the decrease of Hp and the lessening of gastritis.

Japanese Patent Application Kokai No. 4–275232 also discloses the use of specific antibodies, but it merely discloses antibodies obtained from the eggs of hens immunized against Hp whole cells as an antigen. It describes a food for use in prevention of gastritis, gastric ulcer or duodenal ulcer, comprising as an active ingredient antibodies obtained from the eggs of hens immunized with Hp whole cell as an antigen, the antibodies being specific for the antigen, but the effect of the specific antibodies is not clear. The efficacy of the obtained antibodies against whole cells is evaluated by utilizing the fact that Hp adheres to mucin in pig gastric mucosa in vitro, and the results are that egg antibodies against Hp whole cells inhibit the adhesion of Hp to gastric mucosa. However, the in vitro tests were conducted in a mild environment of pH 7.4, and therefore it is questionable whether the obtained data accurately indicate the results to be obtained in a strongly acidic environment of pH 1–3 in the stomach. The confirmation of the effect of eliminating Hp in a strongly acidic stomach requires animals as an Hp infection model in experiments. The above-described patent application does not refer to such experiments, and therefore it is not clear whether the administration of egg antibodies against Hp whole cells can promote the elimination of Hp. Also, there is no reference as to whether the antibodies can suppress the occurrence of gastritis.

It is disclosed in transactions of Japan Agricultural Chemistry Society, 71, pp52, 20p22 (1997) that the egg antibodies against Hp whole cells have an inhibitory effect on Hp growth. However, the antibodies may have the same problems as explained above since the antigen used in immunizing hens is Hp whole cells.

It is known that antibodies against Hp whole cells can be obtained from milk or serum of mammalian animals such as cows. See, Japanese Patent Application Kokai No. 4–169539 and Japanese Patent Application Kokai No. 4–330099. These methods cannot produce antibodies in large amounts and inexpensively. In addition, the antigen used in immunization of mammals is whole cells of Hp, and therefore the complete elimination of Hp is not expected as mentioned in the above Aiba et al. prior art.

As explained above, the long-term use of antibiotics for elimination of Hp results in an increase in antibiotic-resistant bacteria as well as side effects, and a vaccine has not been developed for practical use. Also, attempts to administer lactic acid bacteria or to use egg antibodies against Hp whole cells cannot eradicate Hp, and therefore are not effective for prevention or treatment of gastritis, gastric ulcers and duodenal ulcers.

SUMMARY OF THE INVENTION

It is an object of the present invention to provide a pharmaceutical composition for use in preventing or treating gastritis, gastric ulcers and duodenal ulcers caused by *H. pylori* infection, the composition being effective and safe without the disadvantages of side effects and increase of drug-resistant strains, and to provide a food for preventing these diseases.

It is another object of the present invention to provide specific antibodies for use in preparation of the above pharmaceutical compositions.

Other objects and advantages as well as the nature of the present invention will be apparent from the following description.

The present inventors have found the mechanism of colonization of Hp to gastric mucosa, which mechanism has not been elucidated fully, and completed the present invention based on this discovery.

*H. pylori* cannot grow in an atmospheric condition, grows sub-optimally in an anaerobic condition, and grows optimally in a micro-aerobic condition. Due to this specificity, the ecology of the bacterium in the stomach has not been elucidated. Especially, the reason for strong growth ability in the stomach could not be explained, although various studies have been conducted on the colonization of Hp in gastric mucosa which is the key of growth in the stomach having strong acidity. The colonization of Hp in gastric mucosa plays an important role in the growth of Hp in the stomach, and therefore elucidation of colonization factors is of great significance in developing a method for preventing or treating gastritis, gastric ulcers and duodenal ulcers caused by Hp.

Pathogenic factors of Hp in the stomach have been considered to be urease produced by Hp, flagella for moving freely in the mucosal mucin layer, Cag A outer membrane protein involved in the production of interleukin 8 as an inflammatory cytokine, Vac A vacuolating cytotoxin concerned in vacuolation, erosion, necrosis and ulcer formation of gastric mucosal epithelial cells.

One of the pathogenic factors, urease produced by Hp, has been considered to be able to provide an environment useful for growth of Hp in the stomach by converting urea in the stomach to ammonia and neutralizing a strongly acidic environment around the bacteria cells. On the other hand, with respect to the colonization of Hp in the gastric mucosa, it has been shown that a urease-negative strain of Hp can colonize the stomach as well as a urease-positive strain in experiments using gnotobiotic pigs (Eaton, K. A. and Krakowka, S., 1995, Scand. J. Gastroenterol, 30:434–437). In a recent report, the binding of a urease-negative strain of Hp to human gastric mucosal epithelial cells and to cells from gastric adenocarcinoma cell line (Kato III cells) was compared with the binding of urease-positive strain, and it was concluded that there is no difference between adherence of the two kinds of strains to these cells and that the urease of Hp does not function as an adhesin. (Clyne, M. and Drumm, B. 1996, Infect. Immun. 64:2817–2820)

The present inventors have made the discovery, not expected from the results of prior art studies on the colonization of Hp, that urease itself participates in the colonization of Hp in the gastric mucosa. That is to say, the inventors have found that urease produced by Hp functions as a main adhesin in addition to functioning as an enzyme capable of converting urea to ammonia, and that the binding of urease itself to gastric mucosal mucin enables the growth of Hp. Also, the inventors obtained information suggesting that flagella of Hp also participate in the colonization of Hp in gastric mucosa.

The present invention was made based on the above discovery suggesting that antibodies against whole cells of Hp are not sufficient and antibodies against urease of Hp and/or flagella of Hp are effective for completely inhibiting the colonization of Hp in gastric mucosa to inhibit the growth of Hp in the stomach. It was further found that the combination of each or both of these antibodies and at least one organism selected from lactic acid bacteria, Enterococcuses, yeasts and Bacillus has a synergistic effect.

In one aspect, the present invention provides specific antibodies obtained from eggs laid by hens which have been immunized against urease of *Helicobacter pylori* as an antigen, the specific antibodies being active against the antigen. The present invention also provides specific antibodies obtained from eggs laid by hens which have been immunized against flagella of *Helicobacter pylori* as an antigen, the specific antibodies being active against the antigen.

The above anti-urease antibodies are active against urease, and the above anti-flagella antibodies are active against flagella. Therefore, anti-urease antibodies and/or anti-flagella antibodies are effective for inhibition of *H. pylori* growth in the stomach. The anti-urease antibodies can be used along with at least one organism selected from lactic acid bacteria, Enterococcuses, yeasts, and Bacillus in inhibiting *H. pylori* growth in the stomach. The anti-urease antibodies can be used along with the anti-flagella antibodies and at least one organism selected from lactic acid bacteria, Enterococcuses, yeasts, and Bacillus in inhibiting *H. pylori* growth in the stomach.

In another aspect, the present invention provides a pharmaceutical composition containing as an active ingredient the above-described anti-urease antibodies and/or the above-described anti-flagella antibodies for use in preventing or treating gastritis, gastric ulcer and duodenal ulcer. The anti-urease antibodies can be used along with at least one organism selected from lactic acid bacteria, Enterococcuses, yeasts, and Bacillus in prevention or treatment of gastritis, gastric ulcers and duodenal ulcers. The anti-urease antibodies can be used along with the anti-flagella antibodies and at least one organism selected from lactic acid bacteria, Enterococcuses, yeasts, and Bacillus in prevention or treatment of gastritis, gastric ulcers, and duodenal ulcers.

The present invention also provides a food containing as an additive the above-described anti-urease antibodies and/or the above-described anti-flagella antibodies for use in preventing gastritis, gastric ulcers and duodenal ulcers. To a food containing the anti-urease antibodies, or to a food containing the anti-urease antibodies and the anti-flagella antibodies, at least one organism selected from lactic acid bacteria, Enterococcuses, yeasts, and Bacillus can be added.

DESCRIPTION OF THE PREFERRED EMBODIMENTS

In order to produce the specific antibodies of the present invention, hens are immunized against an antigen. As an antigen to immunize hens, urease and flagella of *H. pylori* are prepared. *H. pylori* strains to be used for preparation of antigens include human clinical isolates such as#130(Cag A+)(Vac A+), NSP#305(Cag A+)(Vac A+), NSP#335(Cag A+)(Vac A+), NSP#355(Cag A–)(Vac A–). After culturing a selected strain, urease component and flagella component are prepared in an appropriate manner.

The immunization of hens against an antigen may be performed by inoculation with the antigen by an appropriate route such as subcutaneous or intramuscular injection. Preferably a suitable adjuvant is administered in conjunction with the antigen to enhance the immunization. Adjuvants useful for this purpose are Freund's complete (incomplete) adjuvant (Difco), Cholera toxin BB (Sigma), Titer Max (CytRx Corp.) etc.

The dose of antigen is determined depending on the type of antigen and adjuvant and the administration route in such a manner that an immune state is induced in the hen without producing excessive toxicity of the antigen therein. Usually, within a few weeks after the inoculation (initial immunization), the hen becomes sensitive to the antigen, i.e., immunized against the antigen. Specific antibodies against the antigen are produced within the body of the hen, and eggs laid by the hen, especially the yolk of the eggs contain the specific antibodies.

After the initial immunization of the hen against the antigen, one or more boosters at an appropriate dose level may be administered in order to maintain a high antibody titer in the hen.

The presence and titer level of the specific antibodies against the antigen in the hen and in eggs of the hen can be confirmed by any method known to those skilled in the art of immunological assays, such as ELISA or a method using agglutination reaction.

After it is confirmed that an adequate titer of the specific antibodies is present in eggs laid by the immunized en, eggs laid by the hen are collected and the desired antibodies are recovered.

The specific antibodies of the present invention may be repared from the overall ovum or the yolk of the eggs. Most antibodies are contained in the yolk of an egg, and usually the yolk is separated from the egg for use in the production of the antibodies. In some cases, overall ovum of the egg may be used.

The overall ovum or the yolk of the egg may be used without fractionation. Alternatively, the overall ovum or the yolk of the egg may be subjected to fractionation or purification. For example, a delipidization procedure may be carried out by suitable methods such as methods using hydroxypropyl methycellurose phthalate, polyethyleneglycol, etc. to remove lipid components from the yolk. If desired, further purification may be carried out by any known method, including known purification procedures of proteins such as salting out with ammonium sulfate or sodium sulfate or cold ethanol precipitation, etc.

The overall ovum or the yolk of the egg, without fractionation or with fractionation or purification, may be used directly or it may be processed. In a preferred embodiment, the overall ovum or the yolk may be stirred or homogenized into an emulsion and dried to form a powder by conventional techniques such as spray drying or lyophilizing. Thus, various forms of antibodies may be used depending on the purpose.

The thus obtained antibodies which are specific for urease or flagella of Hp are effective for eradicating Hp adhered to gastric mucosa and suppressing the occurrence of gastritis in animals for Hp infection model, as demonstrated in the following examples. That is to say, these antibodies can prevent the adhesion of Hp to gastric mucosa and inhibit the growth of Hp in the stomach. These remarkable effects have never been obtained with the prior art antibodies against whole cells of Hp. Additionally, the antibodies from the eggs of hens exhibit superior ability to eliminate Hp to antibodies from mammals, as shown in the following experiment, which is an unexpected result.

Also, when anti-urease antibodies and anti-flagella antibodies are used together, antibodies which have even a somewhat low titer exhibit sufficient effect on eliminating Hp from the stomach and suppressing gastritis due to synergistic effects. Also, when at least one organism selected from lactic acid bacteria, Enterococcuses, yeasts and Bacillus is used along with anti-urease antibodies, or anti-urease antibodies and anti-flagella antibodies, the same effects are exhibited.

Therefore, anti-urease antibodies and/or anti-flagella antibodies are effective for inhibition of Hp in the stomach and can be used for prevention or treatment of gastritis, gastric ulcers, and duodenal ulcers or can be added to a food for prevention of gastritis, gastric ulcers, and duodenal ulcers. These antibodies can be used in combination with at least one organism selected from lactic acid bacteria, Enterococcuses, yeasts and Bacillus in prevention or treatment of these diseases or can be added to a food for prevention of these diseases. The antibodies may be antibody-containing substance recovered directly from the overall ovum or the yolk of the egg from the immunized hen and used as a solution or an emulsion or as a solid such as a powder or granules by drying. Further fractionation or purification of the antibody-containing substance may be carried out to obtain purified antibodies, if desired.

Examples of lactic acid bacteria used in the present invention include *Lactobacillus acidophilus, Lactobacillus gaceri, Lactobacillus cryspatus*, etc. Examples of Enterococcuses are *Enterococcus faecalis, Enterococcus faecium*, etc, examples of yeasts are Candida species, and examples of Bacillus species are *Bacillus subtilis*, etc.

When the specific antibodies of the present invention are used in preventing or treating the above-mentioned diseases, the antibodies can be administered in the form of pharmaceutical composition containing the antibodies and pharmaceutically acceptable carrier therefore. Furthermore, antacids (for example, sodium hydrogencarbonate, magnesium carbonate, precipitated calcium carbonate, synthetic hyrotalsite, etc.), agents for protection of gastric mucosa (for example, aluminium silicate, sucralfate and sodium copper chlorophyllin) and digestive enzymes (biodiastase, lipase, etc.) may be added to the pharmaceutical composition, if necessary or if desired. The preparation of a pharmaceutical composition may be carried out in conventional ways. The administration of the pharmaceutical composition for use in prevention or treatment of these diseases may be done by an oral route.

The dosage of the antibodies of the present invention is selected according to the usage, purpose and conditions of symptoms. Preferably, 0.25–25.0 mg/kg of the purified antibodies may be administered per day for adult in prevention of gastritis, gastric ulcers or dudenal ulcers, and 1.25–125 mg/kg of the purified antibodies may be administered per day for adult in treatment of these diseses.

When the antibodies of the present invention are used as an additive to food for prevention of the above-mentioned diseases, 0.01–0.1 wt % and preferably about 0.05 wt % of purified antibodies may be contained in the food.

The following examples are given to further illustrate the present invention. It should be understood that the present invention is not limited to the specific details set forth in the examples.

EXAMPLE 1

(1) Preparation of Hp Antigens
(i) Preparation of Hp Whole Cell Antigen

Hp#130 strain from a gastritis patient (obtained from the medical college of Tohkai University) was inoculated on brain heart infusion agar medium supplemented with 5% horse blood, and then cultured in a gas pack anaerobic jar at a temperature of 37° C. for 72 hours. After culturing, a smooth colony having a clear gloss and exhibiting weak α-hemolysis was collected and suspended in Brucella broth supplemented with 1–10% fetal bovine serum, and cultured with shaking at a temperature of 37° C. for 24–48 hours while the gas phase was replaced with mixed gas of 10% $CO_2$, 10% $H_2$ and 80% $N_2$. Subculturing was conducted three times to obtain a fourth subculture while the amount of the culture was increased every subculture. Each time a subculture was made, the culture was tested for gram stainability and motility, and a urease test, catalase test, and oxidase test were performed. A fourth subculture obtained by subculturing ($5.2 \times 10^8$ CFU/ml) was centrifuged at 12,000×g for 20 minutes. The cells collected by centrifugation were suspended in sterilized distilled water such that the quantity of culture medium was 100 times less than that of the starting culture medium and then the resulting suspension was treated by a super high-speed homogenizer (Cinematica) at 15,000 rpm for 60 seconds to lyse the cells. it was confirmed that cells were lysed by plating the lysate on an agar medium supplemented with 10% horse blood and observing the growth of the cell.

(ii) Preparation of Flagella Antigen

A culture of HP#130 strain in Brucella broth ($4.0 \times 10^8$ CFU/ml) obtained by the same cultivation procedure as mentioned above was centrifuged at 12,000×g for 20 minutes. The collected cells were suspended in distilled water and stirred by a vortex mixer to remove the urease component. Then, the cells were suspended in tris-HCl buffer (pH 7.2), treated by a super high-speed homogenizer (Cinematica) at 15,000 rpm for 60 seconds, and were centrifuged at 6,700×g for 6 minutes to divide the cells into flagella and remaining parts. To the supernatant containing flagella, trypsin was added (1 mg/ml) and treated at a temperature of 37° C. for 20 minutes to eliminate contaminated protein components such as urease. The flagella-containing fraction was overlaid on a 25–65% sucrose density gradient and centrifugation was carried out at 90,000×g for 22 hours (+4° C.). Then, fractionation was conducted using a fraction collector, and the protein concentration of each fraction was monitored using a densitometer and the presence of flagella was detected using SDS-PAGE. Fractions containing about 50 kDa protein based on this data were pooled, and the pooled fractions were diluted 3–10 fold with distilled water and then centrifuged at 180,000×g for 60 minutes to obtain pellets. The pellets were dissolved in distilled water and then centrifuged at 6,700×g for 2 minutes. The obtained supernatant was subjected to SDS-PAGE, and it was confirmed that it contained flagella A(53 kDa) and flagella B(54 kDa).

(iii) Preparation of Urease Antigen

A culture of Hp#130 in Brucella broth ($3.5 \times 10^8$ CFU/ml) obtained by the same cultivation procedure as mentioned above in (i) was centrifuged at 12,000×g for 20 minutes. The collected cells were suspended in distilled water, stirred by a vortex mixer for 60 seconds, and centrifuged to obtain a supernatant containing urease. Purification was conducted by the following method. The supernatant was applied to a DEAE-Sephacel column equilibrated with a buffer (20 mM phosphate, pH 6.8, 1 mM EDTA, 1 mM 2-mercaptoethanol and 10% PEG 300) and passed through a gel at a flow rate of 0.5 ml/min such that the gel adsorbed urease. Elution was carried out by the 0–0.5 M KCl concentration gradient. Each fraction was monitored with respect to urease activity. The fraction having a peak of urease activity was pooled and concentrated.

Then, the concentrate was applied to a Sephacryl S-300 column equilibrated with a buffer (20 mM phosphate, pH 6.8, 150 mM NaCl), and elution was conducted. The urease activity of each fraction was measured. The fraction having a peak of urease activity was pooled and analyzed using SDS-PAGE to confirm that it contained urease A(32 kDa) and urease B(60 kDa).

(2) Immunization of Hen

Immunization was carried out using white Leghorn, High Line W77 hens about 18 weeks old. Each of three antigens obtained in Example 1 (adjusted to contain 0.5–1.0 mg/ml of protein) was mixed with an oily adjuvant and was injected into the right and left pectoral muscles at a dose of 0.5 ml per injection (initial immunization). Six weeks after the initial immunization, the same antigen was injected as a booster administration in the same manner and at the same dose. About two weeks after the booster injection, the antibody titer of the egg yolk of eggs laid by these mmunized hens increased significantly and become stable, nd then the collection of the eggs was begun and continued or four weeks. With respect to the stability of antibody-producing ability, the antibody titer of the eggs was stable for 4–6 months. After that, the antibody titer decreased, and then the injection was repeated using the same procedure as above to restore the titer.

(3) Assay of the Antibody Titer of Egg Yolk

The yolk was separated from the albumen of each egg and weighed. To this yolk, an equal volume of saline was added to dissolve the yolk component. To this mixture, an equal volume of chloroform was added, and then the mixture was vigorously stirred with shaking and centrifuged. The obtained supernatant was used as a sample for determining the antibody titer. The antibody titer of supernatant was determined by ELISA. The ELISA procedure was as follows. The optimum concentration of immobilized antigen and a conjugate of horseradish peroxidase-fowl IgG was determined by checkerboard titration. A microdilution plate (Immulon 2,Dynex) was used as a plate and an antigen obtained by lysing Hp whole cells was used for immobilizing. An antigen was diluted with carbonate buffer (pH 9.6) so as to contain 5 $\mu$pg/ml of protein, and 100 $\mu$l of the diluted antigen was put into each well and was allowed to stand at 4° C. for 18 hours.

The test procedures were as follows. After each well was washed three times with PBS-Tween, 200$\mu$l of 2% skim milk solution was added for blocking and each well was allowed to stand at 37° C. for 60 minutes. Then, each well was washed three times with PBS-Tween, and lOOml of each sample was added to each well to be allowed to react at 37° C. for 60 minutes. After reaction, the well was washed with PBS-Tween and conjugate diluted 12,000 fold was added in an amount of 100 $\mu$l/well to react at 37° C. for 60 minutes. After each well was washed five times, substrate (o-phenylenediamine hydrochloride containing $H_2O_2$) was added to the well to produce color at room temperature. After 20 minutes, 50 $\mu$l/well of 3N $H_2SO_4$ was added to stop the reaction. Then, absorbance at 490 nm in each well was measured by an ELISA autoreader. The antibody titer of the sample was calculated finally by correcting the measured value on a basis of positive and negative control absorbance.

(4) Preparation of Antibodies from Egg Yolk

After the immunized eggs were washed and disinfected, the yolk was separated from the albumen of each egg, and combined yolk from a plurality of eggs was divided into groups of 8 kg and stored below –20° C. until used. The purification procedures were as follows. To 7.5 kg of the yolk as a starting material was added a 10-fold amount (by weight) of distilled water to delipidize. To the supernatant was added ammonium sulfate to produce 40% saturation. The mixture was stirred and centrifuged to obtain pellets. The pellets were dissolved in saline and 30% saturation salting out was carried out to obtain pellets. The obtained pellets were dissolved in a small amount of water, and to this mixture ethanol at –20° C. was added with stirring so as to give a final concentration of 50%. After centrifugation, the pellets were dissolved in saline and lyophilized. As a result, 11 g of pale yellowish white powder was obtained. The recovery rate of antibodies was about 47%, the purity of IgG was not less than 95%, and the content of water was not more than 2%.

Experiment 1

Efficacy of Various Antibodies From Eggs in Mice Infected with Hp

This experiment was performed to observe whether Hp adhered to gastric mucosa can be eliminated from the stomach, thereby significantly suppressing the occurrence of gastritis, by orally administering egg antibodies against Hp whole cells (comparison experiment), antibodies against urease (the present invention), and antibodies against flagella (the present invention) to a mouse. The mouse was an infection model of a conventional hairless mouse (NS:Hr/ICR) (Research Institute for Human and Animal Propagation, Accession No. IRA-NHI-9701) having a high sensitivity to Hp infection.

Each of hairless mice (male) was challenged with $1\times10^9$ CFU of NSP 335 isolated from clinical material for 3 consecutive days by oral administration. As shown in Table 1, 8 weeks after infection, various antibodies as prepared in Example 1 from the eggs of hens immunized against whole cells, urease of Hp, or flagella of Hp as an antigen were forcefully administered orally once a day for 14 days. After administration for 14 days, mice in each group were sacrificed, blood was collected and the antibody titer against Hp was assayed by ELISA. In necropsy the stomachs of mice of each group were collected and used to count the number of Hp cells in the stomach and to prepare pathological tissue specimens. The number of Hp cells adhered to the gastric mucosa was counted as follows. After completely removing the contents of the stomach, the stomach tissue was washed 8 times with PBS (pH 7.2) and homogenized. The homogenized tissue was placed on a selective medium for detecting Hp (Poremedia Hp isolation medium, Eiken Kagaku) and incubated at 37° C. for 5 days by the gas pack method. Then, the count of viable Hp was conducted. The presence of gastritis was examined by fixing the stomach tissue with formalin and conducting hematoxylin eosin staining in a conventional procedure.

As apparent from the results shown in Table 1, all groups administered egg antibodies exhibited the tendency that Hp in the stomach decreased in a dose-dependent manner. However, the administration of anti-whole cell antibodies could decrease the number of Hp in the stomach only by a factor of about 10 and could not eliminate Hp completely from the stomach. On the contrary, in the group administered anti-flagella antibodies or anti-urease antibodies, Hp in the stomach remarkably decreased in a dose-dependent manner and was almost completely eliminated at a dose of 0.5 ml. This was supported by the antibody titer in the blood determined by ELISA. Thus, the titers in the blood of administered groups were reduced in a dose-dependent manner, and the titers in the blood of the group administered anti-flagella antibodies and the group administered anti-urease antibodies were remarkably low compared to the group administered anti-whole cell antibodies.

Furthermore, it is worthy of attention that although the administration of antibodies against whole cells could decrease Hp in the stomach to some extent, the effect of suppressing the occurrence of gastritis was low, and only one mouse was without gastritis at a dose of 0.5 ml and the rest all had gastritis. In contrast, the administration of anti-flagella antibodies or anti-urease antibodies could suppress the occurrence of gastritis in all mice at a dose of 0.5 ml.

Thus, it was confirmed that the administration of antibodies from eggs of the present invention had superior effects on eradication or clearance of Hp from the stomach and suppressing gastritis in Hp-infected mice.

In the experiments by Aiba et al. mentioned above, Hp #130 from clinical material was given to 4 week-old germ-free BALB/c mice (male) orally at a dose of $1\times10^9$ CFU for 3 days. 4 to 7 weeks after infection, antibodies from eggs against formalin-killed Hp whole cells were administered orally once a day for 14 days and the number of Hp in the stomach was compared with that of the control. As a result, it was shown that the administration of the antibodies against Hp whole cells could decrease the number of Hp in the stomach by a factor of about 10 compared to that of the control group. However, this is not complete elimination. Also, there is no reference to the inhibitory effect on the occurrence of gastritis.

TABLE 1

Effects of Various Egg Antibodies (Ab) Administered to Hp Infected Mice

| Type of Antibody | Dose (ml) | Number of Cells in Stomach (Log 10/g) | | ELISA Antibody Titer in Blood (O.D. Value) | Gastritis |
|---|---|---|---|---|---|
| Comparative | | | | | |
| Anti-Whole Cell | 0.5 | 4.22 ± 0.29** | (5/5)[b] | 0.78 ± 0.32[a] | 4/5[c] |
| Antibody | 0.25 | 4.62 ± 0.07 | (5/5) | 1.16 ± 0.23 | 5/5 |
| (Ab Titer:2560) | 0.1 | 4.90 ± 0.10 | (5/5) | 1.32 ± 0.41 | 5/5 |
| | 0 | 5.08 ± 0.11 | (5/5) | 1.45 ± 0.37 | 5/5 |
| Present Invention | | | | | |
| Anti-Flagella | 0.5 | 0.68 ± 1.24*** | (1/5) | 0.03 ± 0.02*** | 0/5 |
| Antibody | 0.25 | 2.34 ± 1.76** | (3/5) | 0.25 ± 0.33** | 3/5 |
| (Ab Titer:2560) | 0.1 | 4.34 ± 0.24* | (5/5) | 1.09 ± 0.11 | 5/5 |
| | 0 | 5.44 ± 0.27 | (5/5) | 1.40 ± 0.29 | 5/5 |
| Anti-Urease | 0.5 | 0 ± 0*** | (0/5) | 0.07 ± 0.07*** | 0/5 |
| Antibody | 0.25 | 0.76 ± 1.39*** | (1/5) | 0.12 ± 0.11*** | 0/5 |
| (Ab Titer:2560) | 0.1 | 3.78 ± 0.36*** | (5/5) | 0.40 ± 0.12** | 1/5 |
| | 0 | 5.08 ± 0.16 | (5/5) | 1.18 ± 0.28 | 5/5 |

[a]standard derivation
[b]Denominator represents the number of used mice
Numerator represents the number of mice containing Hp in the stomach
[c]Denominator represents the number of used mice
Numerator represents the number of mice positive for gastritis
*$P < 0.05$
**$P < 0.01$
***$P < 0.001$ Experiment 2

Effects of a Combination of Anti-urease Antibodies and Anti-flagella Antibodies from Eggs in Hp-infected Mice This experiment demonstrates synergistic effects obtained by administering anti-urease antibodies and anti-flagella antibodies on elimination of Hp from the stomach.

The procedure of Experiment 1 was repeated except that anti-urease antibodies and anti-flagella antibodies were administered in combination and the amount of administration was 0.1 ml once a day for 14 days. Each mouse in a control group was given 0.1 ml of sterilized saline.

As indicated in Table 2, antibodies to be administered alone were those having an antibody titer of 2,560 and the amount was 0.1 ml. At this dose, anti-urease antibodies could inhibit Hp and suppress gastritis to some extent, and mice administered anti-flagella antibodies showed no significant difference from those in the control group with respect to the number of Hp, and the anti-flagella antibodies had no effect on suppression of gastritis. Nevertheless, the combination of anti-flagella antibodies and anti-urease antibodies could eliminate Hp completely from the stomach and suppress the occurrence of gastritis in all mice, even when the antibodies used had a lower antibody titer of 640.

Thus, the combination of these antibodies exhibits synergistic effects.

TABLE 2

Synergistic Effects when Anti-urease Antibodies and Anti-flagella Antibodies from Eggs were Orally Administered in Combination to Hp-infected Mice

| Type of Antibody | Number of Cells in Stomach (Log 10/g) | | ELISA Antibody Titer (O.D. Value) | Gastritis |
|---|---|---|---|---|
| Anti-Flagella Antibody (2,560)[d] | 4.38 ± 0.26[a] | (5/5)[b] | 1.20 ± 1.15[a] | 5/5[c] |
| Anti-Urease Antibody (2,560) | 3.74 ± 0.33** | (5/5) | 0.45 ± 0.12** | 3/5 |
| Anti-Flagella Antibody (640) + Anti-Urease Antibody (640) | 0 ± 0 | (0/5) | 0.06 ± 0.07*** | 0/5 |
| Control | 5.00 ± 0.27 | (5/5) | 1.21 ± 0.16 | 5/5 |

[a,b,c]see Table 1
[d]Antibody Titer
*$P < 0.01$
***$P < 0.001$

Experiment 3

Synergistic Effects by the Combination of Anti-urease Antibodies and a Lactic Acid Bacterium in Hp-infected Mice
Bhatia, S. J.et al (J. Clin. Microbil., 27:2328–2330, 1989)

stated that *Lactobacillus acidophilus* could inhibit the growth of Hp in vitro and that this inhibitory effect was due to lactic acid. Midolo,P.D. et al. (J. Appl. Bacteriol., 79:475–479, 1995) reported that *Lactobacillus casei, Lactobacillus bulgaricus, Lactobacillus bulgaricus, Pediococcus pentosaceus*, and *Bifidobacterium bifidus* could inhibit the growth of Hp in vitro and this activity was due to organic acids produced by these bacteria. However, these experiments were conducted in vitro and therefore actual results in the stomach cannot be expected.

Also, as mentioned above, Aiba et al. gave Hp#130 isolated from clinical material to 4 week old germ-free BALB/c mice (male) by oral route at a dose of $1 \times 10^9$ CFU for three days, and 4–7 weeks after the infection $1 \times 10^8$ CFU of human *Lactobacillus salivarius* were administered orally for three days. Four weeks after that, mice were sacrificed and the number of Hp in the stomach was compared with that of control group. The number of Hp in the stomach was $1 \times 10^5$ CFU/g in the control group, $10^{2-103}$ CFU/g in the group administered 4 weeks after infection, and $10^4$ CFU/g in the group administered 6 weeks after infection.

Since data by Aiba et al. were obtained using germ-free mice which do not have normal flora in the oral cavity, stomach and intestines, it is questionable if the same results would be obtained in conventional mice having normal flora. Thus, if human lactic acid bacteria are given to conventional mice having inherent normal bacterial flora, they cannot colonize the stomach due to the barrier of mouse inherent bacterial flora.

Experiment 3 was conducted to study the relation between the effect of eliminating Hp from the stomach and the occurrence of gastritis, when human *L. acidophilus* (JCM 1028) was given alone and given along with anti-urease antibodies from eggs to hairless mice having normal bacterial flora. The same experimental procedures as in Experiment 2 were generally used. *L. acidophilus* cultured using Briggs liver broth and cell count was performed by the method of Mitsuoka (1979). $1 \times 10^8$ CFU of the cells were administered once a day for 14 days. As a result, the number of Hp in the stomach of each mouse in the group administered *L. acidophilus* alone was almost the same as that of the control group, and there was no significant difference between the two groups, as shown in Table 3. Also, gastritis conditions were observed and *L. acidophilus* had no efficacy on suppressing gastritis. In this respect, data in this experiment were quite different from data obtained by Aiba et al. using germ-free mice. Thus, the effects of *L. acidophilus* on eliminating Hp from the stomach and suppressing gastritis in mice having normal bacterial flora were not observed. On the contrary, most of Hp was eliminated from the stomach and gastritis conditions were not observed in the group administered *L. acidophilus* and anti-urease antibodies for 14 days. The antibodies used had an antibody titer of 640.

TABLE 3

Synergistic Effects when Anti-urease Antibodies and *L. acidophilus* (JCM 1028) were Administered in Combination Orally to Hp Infected Mice

| Treatment | Number of Cells in Stomach (Log 10/g) | ELISA Antibody Titer (O.D. Value) | Gastritis |
|---|---|---|---|
| *L. acidophilus* ($1 \times 10^9$ CFU)[d] | $4.72 \pm 0.19$[a] | (5/5) $1.17 \pm 0.30$[a] | 5/5[c] |
| Anti-Urease Antibody (2,560)[e] | $3.82 \pm 0.61$** | (5/5) $0.43 \pm 0.05$*** | 3/5 |

TABLE 3-continued

Synergistic Effects when Anti-urease Antibodies and *L. acidophilus* (JCM 1028) were Administered in Combination Orally to Hp Infected Mice

| Treatment | Number of Cells in Stomach (Log 10/g) | ELISA Antibody Titer (O.D. Value) | Gastritis |
|---|---|---|---|
| *L. acidophilus* ($1 \times 10^9$ CFU)[d] + Anti-Urease Antibody (640)[e] | $0 \pm 0$*** | (0/5) $0.03 \pm 0.02$*** | 0/5 |
| Control | $5.24 \pm 0.30$ | (5/5) $1.52 \pm 0.34$ | 5/5 |

[a,b,c]see Table 1
[d]administered cells per mouse
[e]antibody titer per mouse
**$P < 0.01$
***$P < 0.001$ Experiment 4
Comparison of Effects of Anti-urease Antibodies from Eggs and Effects of Anti-urease Antibodies from Serum of Rabbits This experiment demonstrates that antibodies from the eggs of hens are more effective for eliminating Hp from the stomach than antibodies from mammals.

Effects of eliminating Hp were compared when anti-urease antibodies from the eggs of hens and those from serum of rabbits were used respectively. The procedures used were generally the same as in Experiment 2. Antibodies were administered at a dose of 0.5 ml once a day for 14 days.

As shown in Table 4, antibody titers in each mouse in two groups were almost the same, but only in the group administered antibodies from the eggs of hens was Hp eliminated from the stomach completely and was the occurrence of gastritis suppressed. On the contrary. in the group administered antibodies from rabbits, the number of Hp in the stomach decreased only slightly and gastritis was not suppressed. Thus, with respect to the effects of eliminating Hp by passive immunization therapy, it became apparent unexpectedly that egg antibodies which are heterologous to mammals have superior effects to antibodies from mammals.

Antibodies from serum of rabbits as well as antibodies from the eggs of hens did not completely neutralize the enzyme activity of purified urease, although these antibodies were obtained by immunization with urease as an antigen.

TABLE 4

Comparison of Effects when Anti-urease Antibodies from Eggs of Hens and Anti-urease Antibodies from Serum of Rabbits were Orally Administered to Hp-infected Mice

| Antibody Derived From | Number of Cells in Stomach (Log 10/g) | ELISA Antibody Titer (O.D. Value) | Gastritis |
|---|---|---|---|
| Chicken Egg Yolk (2,560)[d] | $0 \pm 0$[a]*** | (0/5)[b] $0.03 \pm 0.01$[a]*** | 0/5[c] |
| Rabbit Serum (2,560)[d] | $4.56 \pm 0.28$ | (5/5) $0.53 \pm 0.23$* | 5/5 |
| Control | $5.10 \pm 0.31$ | (5/5) $1.30 \pm 0.16$ | 5/5 |

[a,b,c,d]see Table 2
*$P < 0.05$
***$P < 0.001$

Experiment 5
Specific Binding of Purified Urease of Hp to Gastric Mucin of Rats

As mentioned above, the results from the previous studies has suggested that urease produced by Hp can provide an environment for growing Hp cells in the stomach by onverting urea to ammonia in the stomach and adjusting the pH to neutral in the region which the cells colonize. Also, he studies by Eaton, K.A. et al. and Clyne, M. et al. has led to the conclusion that urease produced by Hp dose not function as an adhesin for colonization of Hp to gastric mucosa.

However, in the above Experiment 1, anti-urease antibodies from eggs could eliminate colonized Hp from the stomach more effectively than antibodies against other antigens (whole cell antigen and flagella antigen), and suppressed the occurrence of gastritis remarkably. Additionally, the increase of antibody titer against Hp challenge was suppressed by administering anti-urease antibodies. This experiment suggests that urease of Hp is the strongest virulence factor.

Figure 1:
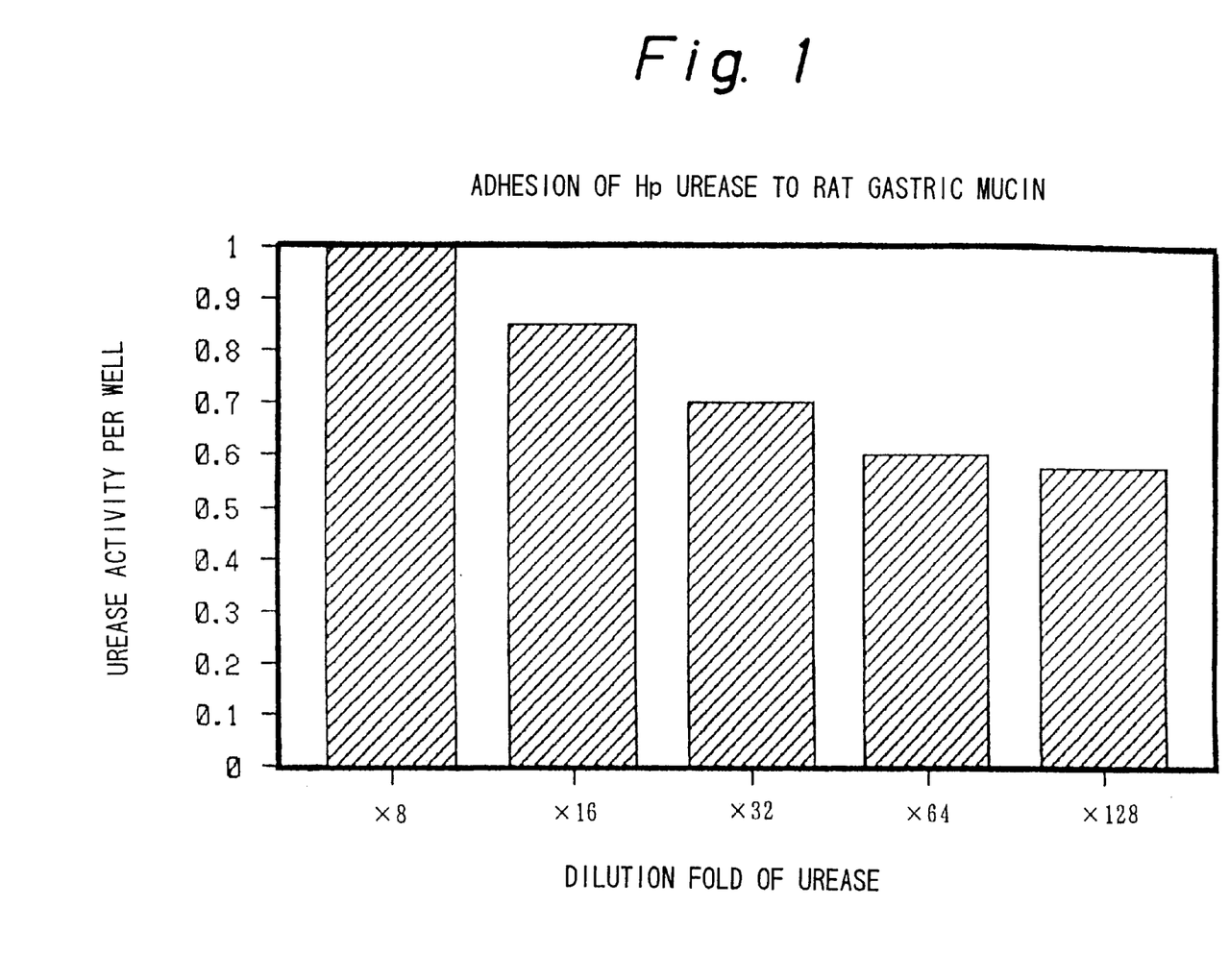
FIG. 1 is a graph indicating that Hp urease binds to rat gastric mucin in a concentration-dependent manner.
Figure 2:
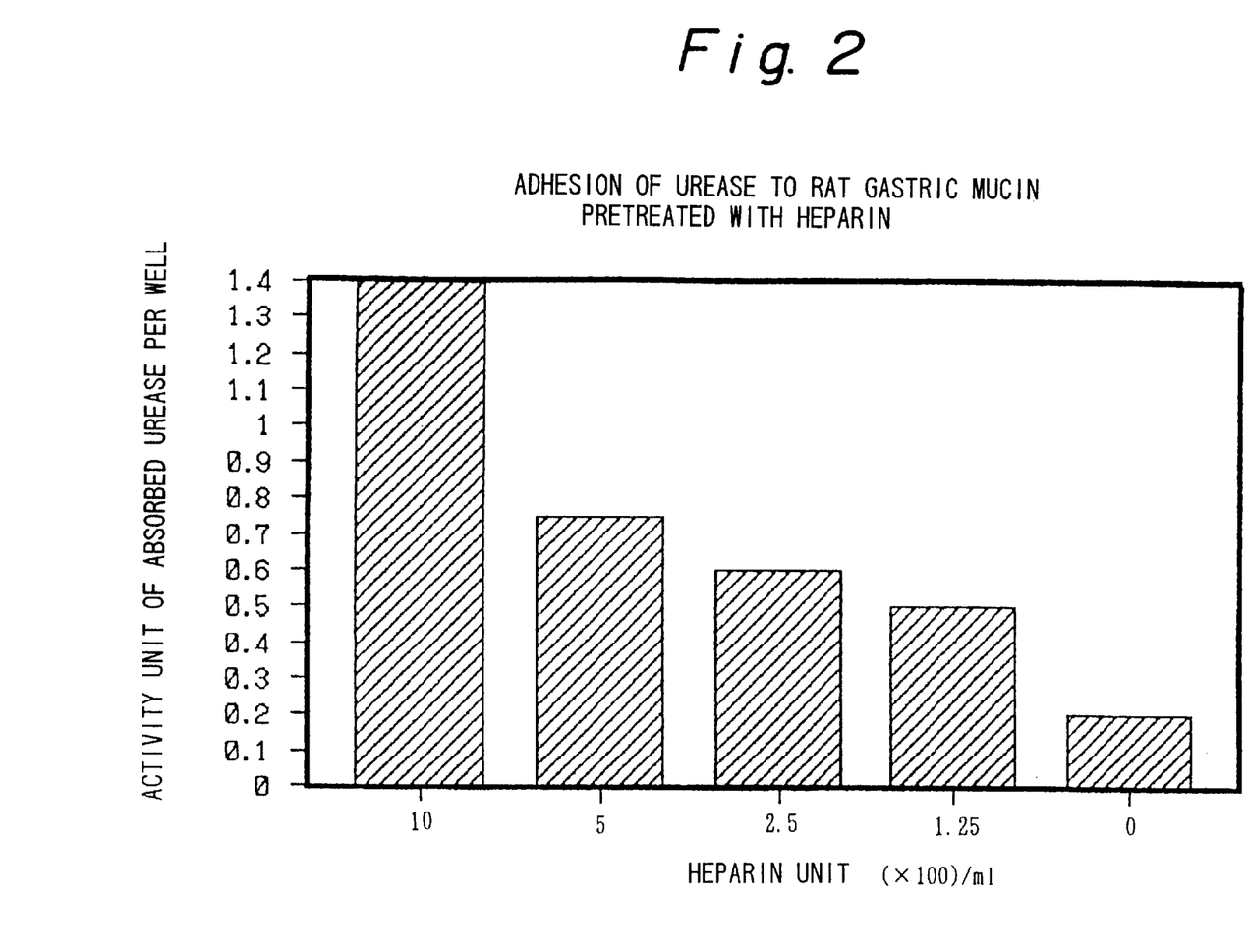
FIG. 2 is a graph showing the binding of urease to rat gastric mucin preadsorbed by heparin.

The present inventors further tested in vitro whether urease of Hp functions as an adhesin to gastric mucosa using purified urease. As a result, urease adhered to rat gastric mucin in a dose-dependent manner as shown in FIG. 1. Then, the experiments indicated in FIG. 2 were conducted to determine the binding site in glycoprotein of mucin to which urease binds, and the obtained results suggest that the binding site is sulfatide in mucin.

Figure 3:
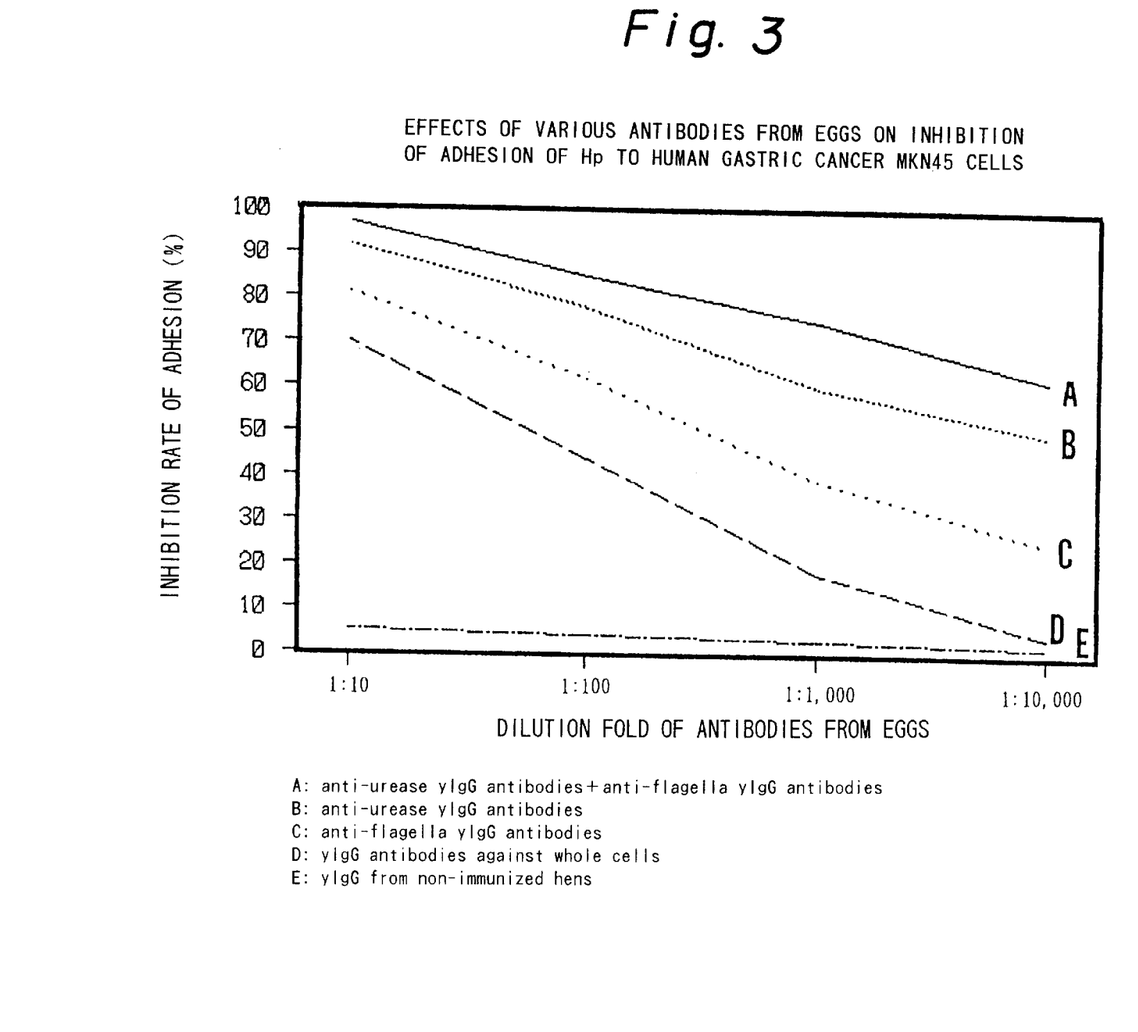
FIG. 3 is a graph showing an inhibitory effect of various antibodies from eggs on adhesion of Hp to human gastric cancer NKM45 cells.

Furthermore, the inhibitory effect of antibodies from eggs on adhesion of Hp to human gastric cancer MKN 45 cells was studied, and it was found that anti-urease antibodies showed the highest inhibitory effect on adhesion of Hp and anti-flagella antibodies showed the next high effect (FIG. 3). Although it has not been confirmed whether purified flagella adhere specifically to rat gastric mucin in fact, there is a considerable possibility that flagella of Hp is concerned with adhesion from the results of Experiment 1.

From the above, it is supposed that since anti-urease antibodies from eggs bind specifically to urease in the surface layer of Hp cells and inhibit the adhesion of Hp to gastric mucin, the antibodies exhibit the highest effect on eliminating Hp in Hp-infected mice. That is to say, urease of Hp functions as an adhesin to gastric mucin.

As is apparent from the above, the present invention provides safe and effective pharmaceutical compositions for use in prevention or treatment of gastritis, gastric ulcers and duodenal ulcers caused by Hp infection, and also provides a food useful for prevention of these diseases. The antibodies of the present invention were obtained based on the discovery of factors contributing colonization of Hp in the stomach, and therefore the antibodies can eradicate Hp of the stomach and effectively suppress gastritis, gastric ulcers and duodenal ulcers. Furthermore, the antibodies are obtained from the eggs of hens according to the present invention, and therefore the desired specific antibodies can be produced in large amounts and inexpensively by simple procedures.

What is claimed is:

1. An antibody composition that inhibits *Helicobacter pylori* adhesion, wherein said antibody composition consists essentially of IgY antibodies that specifically bind to the adhesion portion of *Helicobacter pytori* urease, wherein said IgY antibodies are obtained from at least one chicken egg which has been obtained from a hen that has been immunized with an antigenically effective amount of an immunogen consisting essentially of an isolated *Helicobacter pylori* urease, and wherein said IgY antibodies upon in viva administration to a mammal in an effective amount inhibit *Helicobacter pytori* adhesion in the gastrointestinal tract of said mammal.

2. The antibody composition of claim 1, which further consists essentially of at least one microorganism selected from the group consisting of lactic acid bacterium, Enterococcus, a yeast and a Bacillus.

3. A method for preventing and/or treating a disease caused by or associated with *Helicobacter pylori* in a mammal which comprises orally administering to said mammal a preventive and/or therapeutically effective amount of the antibody composition according to claim 2.

4. A method for preventing and/or treating a disease caused by or associated with *Helicobacter pylori* infection, which comprises orally administering to a mammal a preventive and/or therapeutically effective amount of IgY antibodies according to claim 1.

5. A method for inhibiting *Helicobacter pylori* colonization in the gastrointestinal tract of a mammal which comprises orally administering to said mammal an inhibitory effective amount of IgY antibodies according to claim 1.

6. A pharmaceutical composition suitable for the prevention and/or treatment of at least one of gastritis, gastric ulcers and duodenal ulcers, wherein said pharmaceutical composition consists essentially of:

a pharmaceutically effective amount of IgY antibodies that specifically bind to the adhesion portion of *Helicobacter pylori* urease, wherein said IgY antibodies are obtained from at least one chicken egg which has been obtained from a hen that has been immunized with an antigenically effective amount of an inmunogen consisting essentially of an isolated *Helicobacter pylori* urease, and wherein said IgY antibodies upon in vivo administration to a mammal in an effective amount inhibit *Helicobacter pylori* adhesion in the gastrointestinal tract of said mammal, and a pharmaceutically acceptable carrier or diluent.

7. *Helicobacter pylori* urease IgY antibodies obtained from at least one egg laid by a hen which has been immunized with an antigenically effective amount of an inmunogen consisting essentially of an isolated *Helicobacter pylori* urease, wherein said IgY antibodies specifically bind to the adhesion portion of *Helicobacter pylori* urease in the gastrointestinal tract of a mammal.

8. A food which prevents and/or treats at least one of gastritis, gastric ulcer and duodenal ulcer when consumed in an effective amount, wherein said food comprises a preventive and/or therapeutically effective amount of *Helicobacter pylori* urease IgY antibodies according to claim 7.

9. A food according to claim 8, wherein the amount of said IgY antibodies contained therein range from 0.01 to 0.1% as purified antibodies based on the weight percentage of the food composition.

10. A food according to claim 8, wherein said IgY antibodies are recovered without a fractionation procedure from the ovum or the yolk of eggs of hens which have been immunized against an isolated *Helicobacte[00f8] pylori* urease.

11. An antibody composition that inhibits *Helicobacter pylori* adhesion, wherein said antibody composition comprises *Helicobacter pylori* urease IgY antibodies according to claim 7.

12. A method for inhibiting *Helicobacter pylori* urease as an adhesin for colonization in the gastrointestinal tract of a mammal which comprises orally administering to said mammal an inhibitory effective amount of IgY antibodies which specifically bind to the adhesion portion of *Helicobacter pylori* urease, wherein said IgY antibodies are obtained from at least one egg laid by a hen which has been immunized with an antigenically effective amount of an immunogen consisting essentially of an isolated *Helicobacter pylori* urease.

13. A method for preventing and/or treating a disease caused by or associated with *Helicobacter pylori* in a mammal which comprises inhibiting *Helicobacter pylori* urease as an adhesin for colonization in the gastrointestinal tract of the mammal by orally administering to said mammal a preventive and/or therapeutically effective amount of IgY antibodies which specifically bind to the adhesion portion of *Helicobacter pylori* urease, wherein said IgY antibodies are obtained from at least one egg laid by a hen which has been immunized with an antigenically effective amount of an immunogen consisting essentially of an isolated *Helicobacter pylori* urease.

14. Isolated and purified *Helicobacter pylori* urease IgY antibodies which specifically bind to the adhesion portion of *Helicobacter pylori* urease in the gastrointestinal tract of a mammal, wherein said isolated and purified antibodies are isolated and purified from at least one egg laid by a hen which has been irnnunized with an antigenically effective amount of an immunogen consisting essentially of an isolated *Helicobacter pylori* urease.

15. A method for inhibiting *Helicobacter pylori* urease as an adhesin for colonization in the gastrointestinal tract of a mammal which comprises orally administering to said mammal an inhibitory effective amount of isolated and purified IgY antibodies which specifically bind to the adhesion portion of *Helicobacter pylori* urease, wherein said isolated and purified antibodies are isolated and purified from at least one egg laid by a hen which has been immunized with an antigenically effective amount of an inmunogen consisting essentially of an isolated *Helicobacter pylori* urease.

16. A method for preventing and/or treating a disease caused by or associated with *Helicobacter pylori* in a mammal which comprises inhibiting *Helicobacter pylori* urease as an adhesin for colonization in the gastrointestinal tract of the mammal by orally administering to said mammal a preventive and/or therapeutically effective amount of isolated and purified IgY antibodies which specifically bind to the adhesion portion of *Helicobacter pylori* urease, wherein said isolated and purified antibodies are isolated and purified from at least one egg laid by a hen which has been immunized with an antigenically effective amount of an immunogen consisting essentially of an isolated *Helicobacter pylori* urease.

17. A *Helicobacter pylori* urease IgY antibody containing egg laid by a hen produced by the process of immunizing said hen with an antigenically effective amount of an immunogen consisting essentially of an isolated *Helicobacter pylori* urease, wherein said IgY antibodies specifically bind to the adhesion portion of *Helicobacter pylori* urease in the gastrointestinal tract of a mammal.

* * * * *